(12) United States Patent
Granger et al.

(10) Patent No.: US 11,134,946 B2
(45) Date of Patent: Oct. 5, 2021

(54) STAPLE CARTRIDGE AND METHODS FOR SURGICAL STAPLERS

(71) Applicant: Bolder Surgical, LLC, Louisville, CO (US)

(72) Inventors: Richard N. Granger, Niwot, CO (US); Allison B. Lyle, Boulder, CO (US); Joseph D. Bucciaglia, Boulder, CO (US)

(73) Assignee: Bolder Surgical, LLC, Louisville, CO (US)

( * ) Notice: Subject to any disclaimer, the term of this patent is extended or adjusted under 35 U.S.C. 154(b) by 232 days.

(21) Appl. No.: 16/285,597

(22) Filed: Feb. 26, 2019

(65) Prior Publication Data

US 2019/0261983 A1  Aug. 29, 2019

Related U.S. Application Data

(60) Provisional application No. 62/636,025, filed on Feb. 27, 2018.

(51) Int. Cl.
*A61B 17/072* (2006.01)
*A61B 17/00* (2006.01)

(52) U.S. Cl.
CPC ............. *A61B 17/07207* (2013.01); *A61B 2017/00991* (2013.01); *A61B 2017/07221* (2013.01); *A61B 2017/07228* (2013.01); *A61B 2017/07257* (2013.01); *A61B 2017/07271* (2013.01); *A61B 2017/07278* (2013.01); *A61B 2017/07285* (2013.01)

(58) Field of Classification Search
None
See application file for complete search history.

(56) References Cited

U.S. PATENT DOCUMENTS 6,840,945 B2  1/2005  Manetakis et al.
6,872,214 B2  3/2005  Sonnenschein et al.
(Continued)

FOREIGN PATENT DOCUMENTS

EP  3097866 A1  11/2016
WO  WO2017003926 A1  1/2017
(Continued)

OTHER PUBLICATIONS

Kim, Yeonkyung, International Search Report, dated Jul. 2, 2019, 3 pages, Korean Intellectual Property Office, Republic of Korea.
(Continued)

*Primary Examiner* — Anna K Kinsaul
*Assistant Examiner* — Chinyere J Rushing-Tucker
(74) *Attorney, Agent, or Firm* — Schneider IP Law LLC; Laura A. Schneider

(57) ABSTRACT

A surgical stapler, cartridge assembly, and related methods are disclosed. A cartridge assembly for a surgical stapler has a first cartridge portion; and a second cartridge portion; wherein each of the first and second cartridge portions has an upper surface for engaging tissue, and a slot to house a staple. A proximal portion of each of the first and second cartridge portions has a guide portion having at least one of a channel or a protrusion for guiding at least a portion of an i-beam. The second cartridge portion is removably couplable to the first cartridge portion to form a channel.

14 Claims, 22 Drawing Sheets

(56) References Cited

U.S. PATENT DOCUMENTS

| | | |
|---|---|---|
| 6,959,852 B2 | 11/2005 | Shelton, IV et al. |
| 6,989,016 B2 | 1/2006 | Tallarida et al. |
| 7,044,352 B2 | 5/2006 | Shelton, IV et al. |
| 7,048,171 B2 | 5/2006 | Kosted |
| 7,121,446 B2 | 10/2006 | Arad et al. |
| 7,143,923 B2 | 12/2006 | Shelton, IV et al. |
| 7,188,758 B2 | 3/2007 | Viola et al. |
| 7,261,724 B2 | 8/2007 | Molitor et al. |
| 7,326,232 B2 | 2/2008 | Viola et al. |
| 7,334,717 B2 | 2/2008 | Rethy et al. |
| 7,357,287 B2 | 4/2008 | Shelton, IV et al. |
| 7,380,695 B2 | 6/2008 | Doll et al. |
| 7,399,310 B2 | 7/2008 | Edoga et al. |
| 7,407,075 B2 | 8/2008 | Holsten et al. |
| 7,434,715 B2 | 10/2008 | Shelton, IV et al. |
| 7,487,899 B2 | 2/2009 | Shelton, IV et al. |
| 7,552,854 B2 | 6/2009 | Wixey et al. |
| 7,556,186 B2 | 7/2009 | Milliman |
| 7,568,605 B2 | 8/2009 | Kruszynski |
| 7,575,144 B2 | 8/2009 | Ortiz et al. |
| 7,588,177 B2 | 9/2009 | Racenet |
| 7,597,229 B2 | 10/2009 | Boudreaux et al. |
| 7,604,151 B2 | 10/2009 | Hess et al. |
| 7,617,961 B2 | 11/2009 | Viola |
| 7,631,793 B2 | 12/2009 | Rethy et al. |
| 7,641,092 B2 | 1/2010 | Kruszynski et al. |
| 7,641,093 B2 | 1/2010 | Doll et al. |
| 7,690,547 B2 | 4/2010 | Racenet et al. |
| 7,726,537 B2 | 6/2010 | Olson et al. |
| 7,731,072 B2 | 6/2010 | Timm et al. |
| 7,731,073 B2 | 6/2010 | Wixey et al. |
| 7,735,703 B2 | 6/2010 | Morgan et al. |
| 7,753,246 B2 | 7/2010 | Scirica |
| 7,810,693 B2 | 10/2010 | Broehl et al. |
| 7,815,092 B2 | 10/2010 | Whitman et al. |
| 7,819,296 B2 | 10/2010 | Hueil et al. |
| 7,819,299 B2 | 10/2010 | Shelton, IV et al. |
| 7,866,525 B2 | 1/2011 | Scirica |
| 7,926,692 B2 | 4/2011 | Racenet et al. |
| 7,934,629 B2 | 5/2011 | Wixey et al. |
| 7,942,300 B2 | 5/2011 | Rethy et al. |
| 7,942,303 B2 | 5/2011 | Shah |
| 7,950,562 B2 | 5/2011 | Beardsley et al. |
| 7,959,051 B2 | 6/2011 | Smith et al. |
| 7,967,180 B2 | 6/2011 | Scirica |
| 7,988,028 B2 | 8/2011 | Farascioni et al. |
| 8,007,513 B2 | 8/2011 | Nalagatla et al. |
| 8,008,598 B2 | 8/2011 | Whitman et al. |
| 8,015,976 B2 | 9/2011 | Shah |
| 8,028,884 B2 | 10/2011 | Sniffin et al. |
| 8,033,438 B2 | 10/2011 | Scirica |
| 8,033,440 B2 | 10/2011 | Wenchell et al. |
| 8,061,577 B2 | 11/2011 | Racenet et al. |
| 8,070,034 B1 | 12/2011 | Knodel |
| 8,123,101 B2 | 2/2012 | Racenet et al. |
| 8,141,762 B2 | 3/2012 | Bedi et al. |
| 8,276,594 B2 | 10/2012 | Shah |
| 8,393,513 B2 | 3/2013 | Jankowski |
| 8,408,442 B2 | 4/2013 | Racenet et al. |
| 8,469,254 B2 | 6/2013 | Czernik et al. |
| 8,496,155 B2 | 7/2013 | Knodel |
| 8,540,133 B2 | 9/2013 | Bedi et al. |
| 8,596,513 B2 | 12/2013 | Olson et al. |
| 8,701,959 B2 | 4/2014 | Shah |
| 8,800,840 B2 | 8/2014 | Jankowski |
| 8,800,841 B2 | 8/2014 | Ellerhorst et al. |
| 9,016,539 B2 | 4/2015 | Kostrzewski et al. |
| 9,089,326 B2 | 7/2015 | Krumanaker et al. |
| 9,179,911 B2 | 11/2015 | Morgan et al. |
| 9,433,411 B2 | 9/2016 | Racenet et al. |
| 9,510,827 B2 | 12/2016 | Kostrzewski |
| 9,566,062 B2 | 2/2017 | Boudreaux |
| 9,724,096 B2 | 8/2017 | Thompson et al. |
| 9,782,171 B2 | 10/2017 | Viola |
| 9,814,463 B2 | 11/2017 | Williams et al. |
| 9,820,741 B2 | 11/2017 | Kostrzewski |
| 9,820,742 B2 | 11/2017 | Covach et al. |
| 9,848,878 B2 | 12/2017 | Racenet et al. |
| 9,872,683 B2 | 1/2018 | Hopkins et al. |
| 2005/0021027 A1 | 1/2005 | Shields et al. |
| 2007/0027469 A1 | 2/2007 | Smith et al. |
| 2011/0245578 A1* | 10/2011 | Wazer .................. A61N 5/1027 600/3 |
| 2012/0292369 A1* | 11/2012 | Munro, III ....... A61B 17/07207 227/176.1 |
| 2013/0008937 A1 | 1/2013 | Viola |
| 2013/0087599 A1 | 4/2013 | Krumanaker et al. |
| 2013/0098969 A1 | 4/2013 | Scirica et al. |
| 2013/0284791 A1 | 10/2013 | Olson et al. |
| 2013/0334283 A1 | 12/2013 | Swayze et al. |
| 2013/0334285 A1 | 12/2013 | Swayze et al. |
| 2014/0021239 A1* | 1/2014 | Kostrzewski .... A61B 17/07207 227/175.3 |
| 2014/0103092 A1* | 4/2014 | Kostrzewski .... A61B 17/07207 227/178.1 |
| 2014/0239037 A1 | 8/2014 | Boudreaux et al. |
| 2014/0252061 A1 | 9/2014 | Estrella et al. |
| 2014/0263558 A1 | 9/2014 | Hausen et al. |
| 2014/0263570 A1* | 9/2014 | Hopkins .......... A61B 17/07207 227/180.1 |
| 2014/0284372 A1* | 9/2014 | Kostrzewski .... A61B 17/07207 227/177.1 |
| 2015/0157321 A1 | 6/2015 | Zergiebel et al. |
| 2015/0282807 A1 | 10/2015 | Chen et al. |
| 2015/0327862 A1* | 11/2015 | Kostrzewski .... A61B 17/07207 227/178.1 |
| 2016/0106452 A1 | 4/2016 | Duperier et al. |
| 2016/0128694 A1 | 5/2016 | Baxter, III et al. |
| 2016/0199088 A1 | 7/2016 | Shelton, IV et al. |
| 2016/0235409 A1 | 8/2016 | Shelton, IV et al. |
| 2016/0256159 A1 | 9/2016 | Pinjala et al. |
| 2016/0256167 A1 | 9/2016 | Kostrzewski et al. |
| 2016/0262751 A1 | 9/2016 | Petty et al. |
| 2016/0262758 A1 | 9/2016 | Olson et al. |
| 2016/0270788 A1* | 9/2016 | Czernik ................ A61B 17/105 |
| 2016/0270790 A1 | 9/2016 | Jankowski |
| 2016/0278779 A1 | 9/2016 | Jankowski |
| 2016/0345971 A1 | 12/2016 | Bucciaglia et al. |
| 2016/0345973 A1* | 12/2016 | Marczyk .......... A61B 17/07207 |
| 2016/0354085 A1 | 12/2016 | Shelton, IV et al. |
| 2017/0007236 A1 | 1/2017 | Shelton, IV et al. |
| 2017/0020525 A1 | 1/2017 | Shah |
| 2017/0025517 A1 | 1/2017 | Tang et al. |
| 2017/0055991 A1 | 3/2017 | Kang |
| 2017/0216494 A1 | 8/2017 | Roth et al. |
| 2017/0231633 A1 | 8/2017 | Marczyk et al. |
| 2017/0319777 A1 | 11/2017 | Shelton, IV et al. |
| 2017/0360441 A1 | 12/2017 | Sgroi |
| 2018/0125485 A1 | 5/2018 | Beardsley et al. |
| 2018/0250006 A1 | 9/2018 | Bucciaglia et al. |

FOREIGN PATENT DOCUMENTS

| | | |
|---|---|---|
| WO | WO2017100257 A1 | 6/2017 |
| WO | 2019/168808 | 9/2019 |

OTHER PUBLICATIONS

Kim, Yeonkyung, Written Opinion, dated Jul. 2, 2019, 7 pages, Korean Intellectual Property Office, Republic of Korea.

Kim, Yeonkyung "International Search Report and Written Opinion for PCT/US2019/019493," dated Jul. 2, 2019, 10 pages, published in: Korea.

Kim, Yeonkyung "International Preliminary Report on Patentability for PCT/US2019/019493," dated Aug. 27, 2020, 8 pages, published in: Korea.

Tecco, Andrew M., Office Action in Response to U.S. Appl. No. 15/968,819, dated May 29, 2019, 27pp.

(56) References Cited

OTHER PUBLICATIONS

Tecco, Andrew M., Office Action in Response to U.S. Appl. No. 15/968,819, dated Dec. 12, 2018, 206pp.

* cited by examiner

US 11,134,946 B2

STAPLE CARTRIDGE AND METHODS FOR SURGICAL STAPLERS

CLAIM OF PRIORITY

This application claims priority to U.S. Provisional Application No. 62/636,025 filed on Feb. 27, 2018 and entitled "Staple Cartridge and Methods for Surgical Staples," the entire disclosure of which is hereby incorporated by reference for all proper purposes.

BACKGROUND

Field

The present invention relates generally to surgical staplers, and more specifically to cartridges for surgical staplers.

Background

Historically, surgical staplers have been provided with a cartridge having a unitary piece for supporting staples prior to application to a patient. More recently, however, the surgical industry has become more focused on reducing the size of the tools, and, increasingly, it has been determined that simply reducing dimensions often does not result in a functional tool. A complete re-thinking of mechanisms to provide a small or micro-sized tool is needed, and improvements in manufacturability and reliability are desired, as are other new and innovative features.

SUMMARY

A cartridge assembly for a surgical stapler has a first cartridge portion and a second cartridge portion. Each of the first and second cartridge portions has an upper surface for engaging tissue, and a slot configured to house a staple. A proximal portion of each of the first and second cartridge portions has a guide portion having at least one of a channel or a protrusion for guiding at least a portion of an i-beam. The second cartridge portion is removably couplable to the first cartridge portion to form a channel between the first and second cartridge portion.

A surgical stapler has a cartridge assembly, the cartridge assembly having a first cartridge portion and a second cartridge portion, wherein each of the first and second cartridge portions has an upper surface for engaging tissue, and a slot to house a staple, a proximal portion of each of the first and second cartridge portions has a guide portion having at least one of a channel or a protrusion for guiding at least a portion of an i-beam. The second cartridge portion is removably couplable to the first cartridge portion to form a channel between the first and second cartridge portion. The stapler also has a distal cap and a housing. The distal cap and the housing removably couple the first cartridge portion and the second cartridge portion to form a channel therebetween.

A method of making a surgical stapler includes providing a cartridge assembly, the cartridge assembly having a first cartridge portion, and a second cartridge portion, wherein each of the first and second cartridge portions has an upper surface for engaging tissue, and a slot to house a staple. A proximal portion of each of the first and second cartridge portions has a guide portion having at least one of a channel or a protrusion for guiding at least a portion of an i-beam. The second cartridge portion is removably couplable to the first cartridge portion to form a channel between the first and second cartridge portion. The method includes providing a distal cap and providing a housing, and using the distal cap and the housing to removably couple the first cartridge portion and the second cartridge portion and form a channel therebetween.

DETAILED DESCRIPTION

Figure 1:
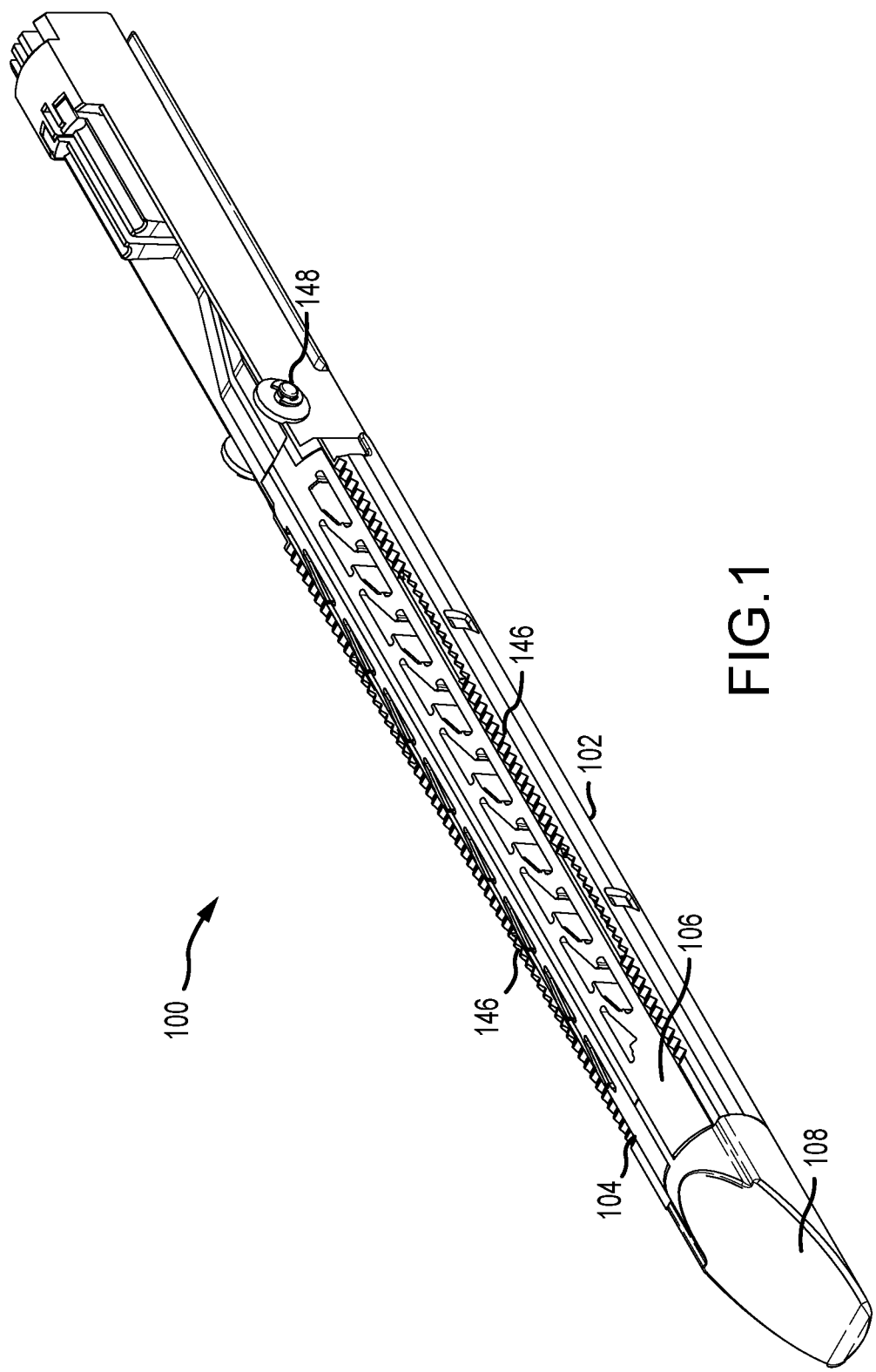
FIG. 1 is a perspective view of a cartridge assembly.
Figure 2:
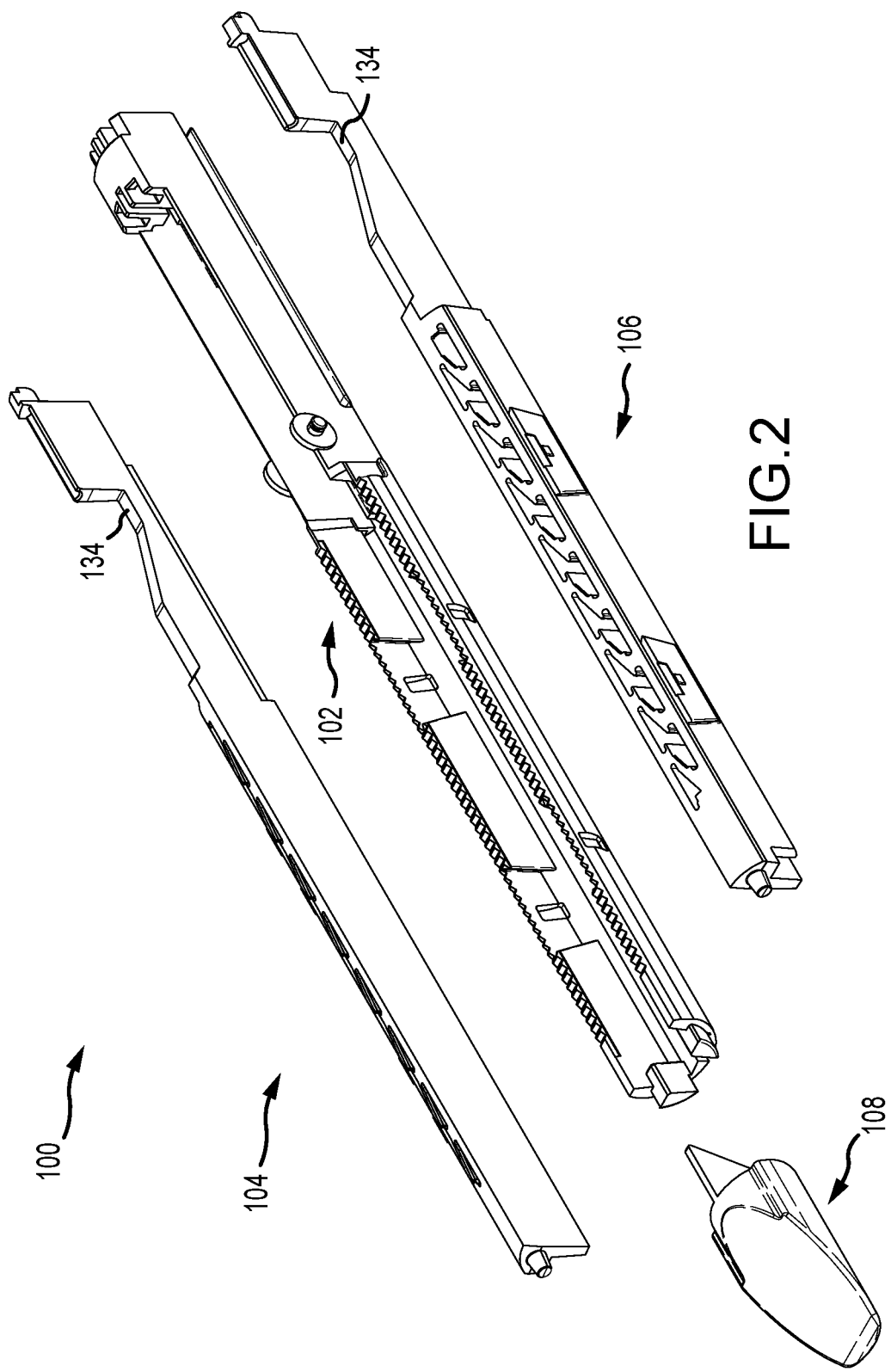
FIG. 2 is a perspective exploded view of the assembly in FIG. 1.

Turning first to FIG. 1 and FIG. 2, embodiments of a cartridge assembly 100 for a surgical stapler are now described herein. A cartridge assembly 100 may have a housing 102 for seating or housing a first cartridge portion 104 and a second cartridge portion 106. The first and second cartridge portions 104, 106 may be coupled to each other and/or the housing 102 by a cap 108. The first and second cartridge portions 104, 106 may be shaped and configured to form a channel 118 therebetween. For example, inner walls 118a, 118b of the first and second cartridge portions 104, 106 may form a channel 118 therebetween. With brief reference to FIG. 8, in some embodiments, the slot 116 for housing a staple and/or staple pusher in at least one of the first or second cartridge portions 104, 106 may be configured to house a staple at a non-parallel angle to an inner wall 118a, 118b of the cartridge portion 104, 106 that forms the channel 118. The channel 118 may be referenced herein as a knife channel 118; however, those skilled in the art will recognize that the knife channel 118 may be suited for allowing translation of features besides a knife.

Returning now to FIG. 3, FIG. 4, and FIG. 5, the cartridge assembly 100 may include first and second cartridge portions 104, 106 that are substantially mirror images of each other. Each cartridge portion 104, 106 may include a recess 116 or series of recesses for housing one or more staples (not illustrated) and staple pushers (not illustrated). One or both recesses 116 may be shaped and configured to house staples at a non-parallel angle to the knife channel 118, as most clearly illustrated in FIG. 8 and FIG. 9. The angle may be less than about 8 degrees. The angle may be less than about 5 degrees.

Figure 3:
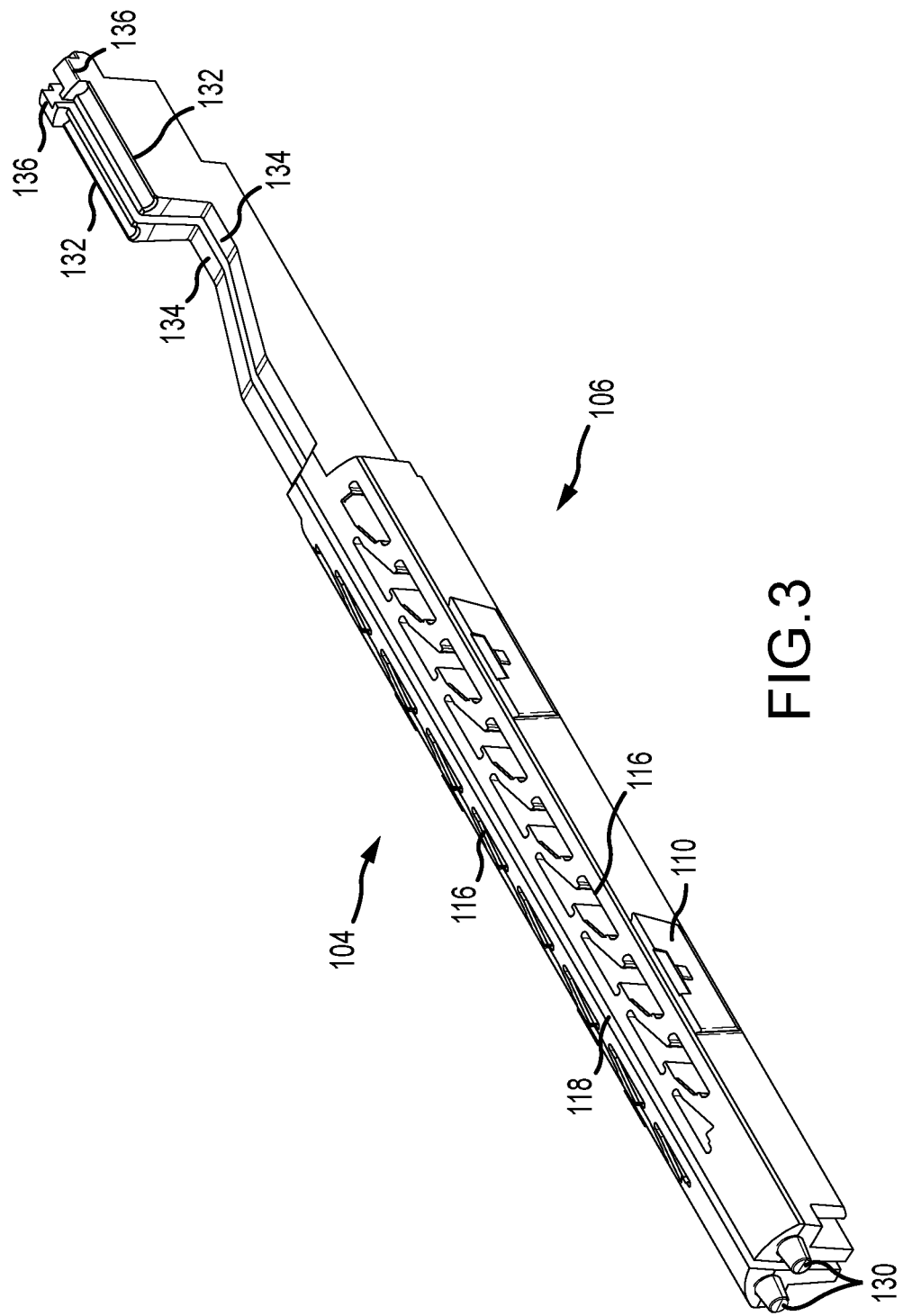
FIG. 3 is a perspective view of a cartridge assembly.

FIG. 3 illustrates a perspective view of a 2-piece cartridge according to some embodiments. In some embodiments, a 2-piece cartridge may include a first cartridge portion configured to be positioned adjacent to or coupled to a second cartridge portion. In some embodiments, a housing may serve a coupling function to position the first and cartridge portions relative to each other. In some embodiments, the first and second cartridge portions are unitary with each other. In some embodiments, the first and second cartridge portions are configured to receive an I-beam therebetween. In some embodiments, the first and second cartridge portions are molded. In some embodiments, the first and second cartridge portions are coupled together prior to fixing to a housing. In some embodiments, one or both of the cartridge portions include alignment features, to align the respective cartridge portion(s) to the housing and/or to the other cartridge portion.

Figure 6:
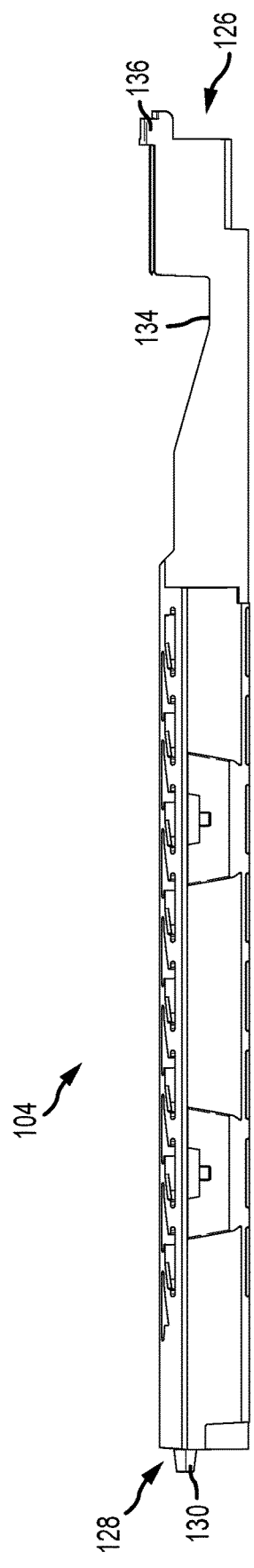
FIG. 6 is a first side view of a first cartridge portion illustrated in the assembly in FIG. 3.

As illustrated most clearly in FIG. 6 and FIG. 3, one or both cartridge portions 104, 106 may have a proximal portion 126 and a distal portion 128, with a recess 134 therebetween. The recess 134 may be shaped and configured to receive and/or allow a proximal portion of an anvil to move into the recess 134. The proximal portion 126 may include a guide 132 for guiding a portion of an i-beam. For example, the guide 132 may be a channel as illustrated to engage a raised portion of the i-beam portion 182 (see e.g. FIG. 28). The i-beam portion 182 may include or be coupled to a knife 180 and a lower i-beam portion 184. In some embodiments, the i-beam may be an expanding i-beam.

The proximal portion 126 of one or both cartridge portions 104, 106 may include a tab 135, flange, or engagement feature for engaging the cartridge housing 102.

Figure 8:
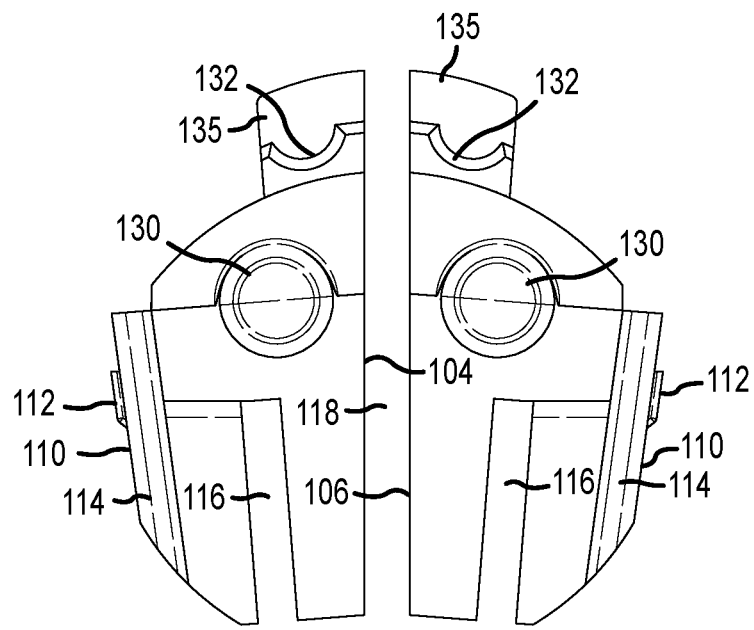
FIG. 8 is a distal end view of the assembly in FIG. 3.
Figure 9:
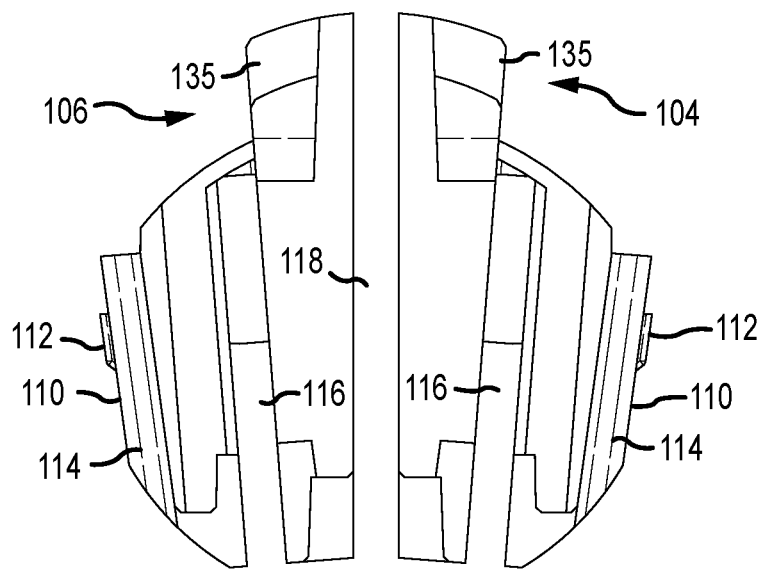
FIG. 9 is a proximal end view of the assembly in FIG. 3.

As best illustrated in FIG. 2, FIG. 6, and FIG. 8, one or both of the cartridge portions 104, 106 may include one or more alignment features 130, which may be protrusions 130 to engage a distal cap 108.

In some embodiments, a method may include providing a cartridge housing 102, affixing a first cartridge portion 104 and a second cartridge portion 106, and attaching a distal cap 108 to prevent the cartridge portions 104, 106 from being removed or moving during I-beam deployment.

Figure 7:
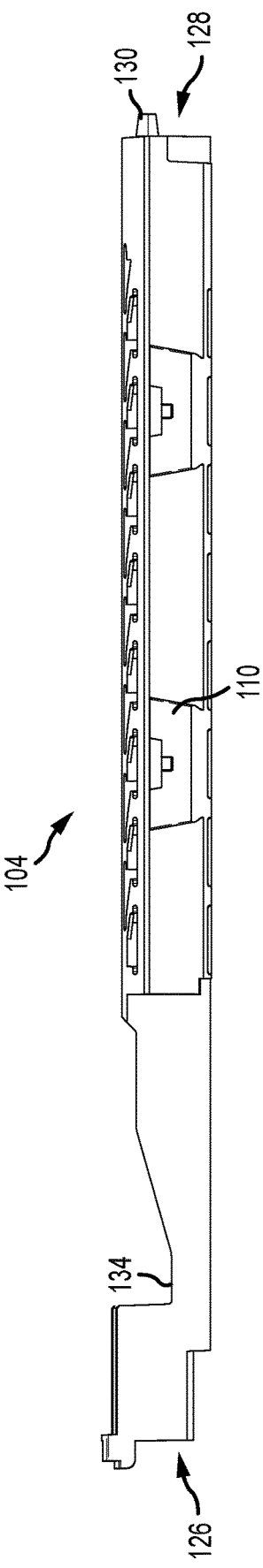
FIG. 7 is a second side view of the first cartridge portion illustrated in the assembly in FIG. 3.
Figure 7A:
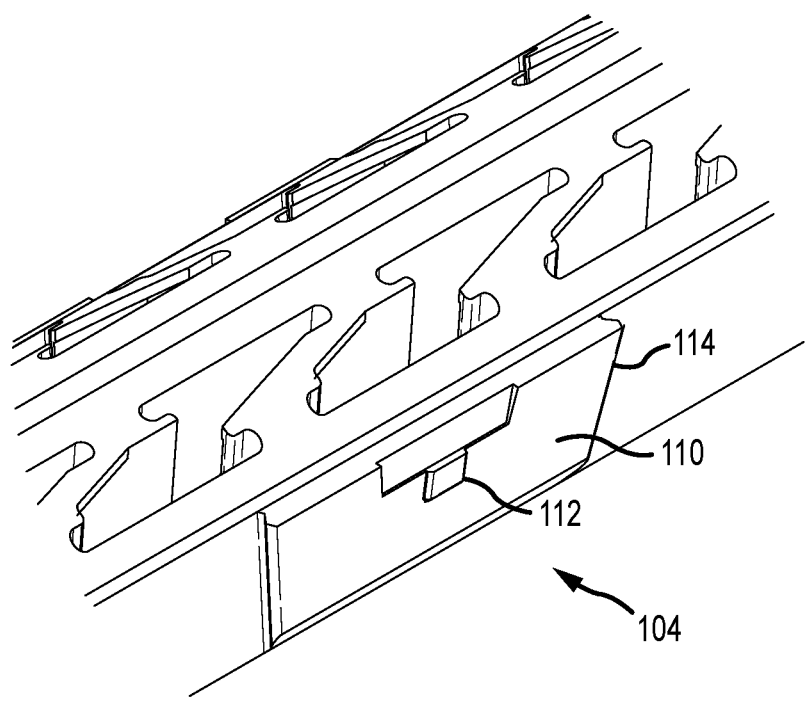
FIG. 7A is a detailed view of a feature of the first cartridge portion illustrated in FIG. 7.

As illustrated in FIG. 7 and FIG. 7A, one or both cartridge portions 104, 106 may include an alignment feature 110 for aligning the respective cartridge portion 104, 106 to the housing 102. The alignment feature 110 may include a flange 114 for engaging a respective flange 120 in the housing 102. See FIG. 13 for an illustration of the flange 120 in the housing 102. The alignment feature 110 may include a tab 112 for engaging a recess and respective flange surface 122 in the housing 102, to prevent the cartridge 104, 106 from inadvertent removal from the housing 102 or moving during I-beam deployment.

Although not illustrated, those skilled in the art will recognize that the first and second cartridge portions may include one or more flanges and/or other coupling means to interlock or couple the cartridge portions 104, 106 to each other. The coupling means may include cartridge housing and/or a cap.

In some embodiments, the tab 112 may be manually depressed to cause the tab 112 to deflect and disengage from the flange surface 122 to allow the cartridge portion 104, 106 to be removed.

Figure 10:
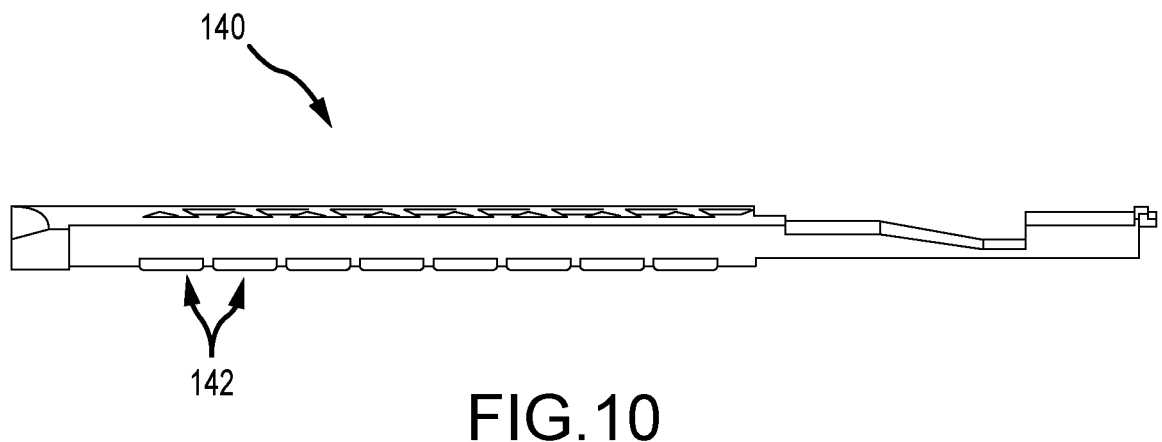
FIG. 10 is a side perspective view of a cartridge component having options suitable for use in the cartridge assembly of FIG. 3.
Figure 11:
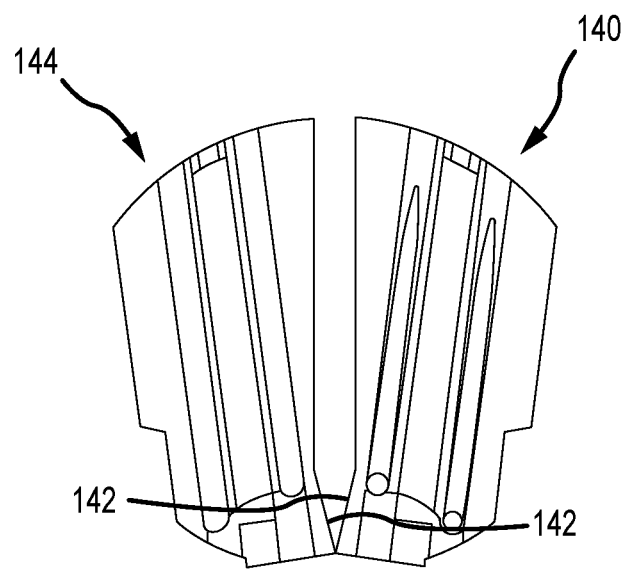
FIG. 11 is a section view illustrating features of the component in FIG. 10.

Turning now to FIG. 10 and FIG. 11, in some embodiments, one or both cartridge portions 140, 144 may have movable channel portions 142. The movable channel portions 142 may be displaced as a knife (not illustrated) is translated through the knife channel The movable channel portions 142 may be resilient portions of the cartridge portion(s) 140, 144, and may move into space previously occupied by a staple and/or staple pusher. That is, the device may be configured to translate a cam to cause movement of the staple pusher and/or staple, and, thereafter, the knife may translate through the knife channel to widen at least a portion of the knife channel by displacing the movable channel portion(s) 142.

Figure 12:
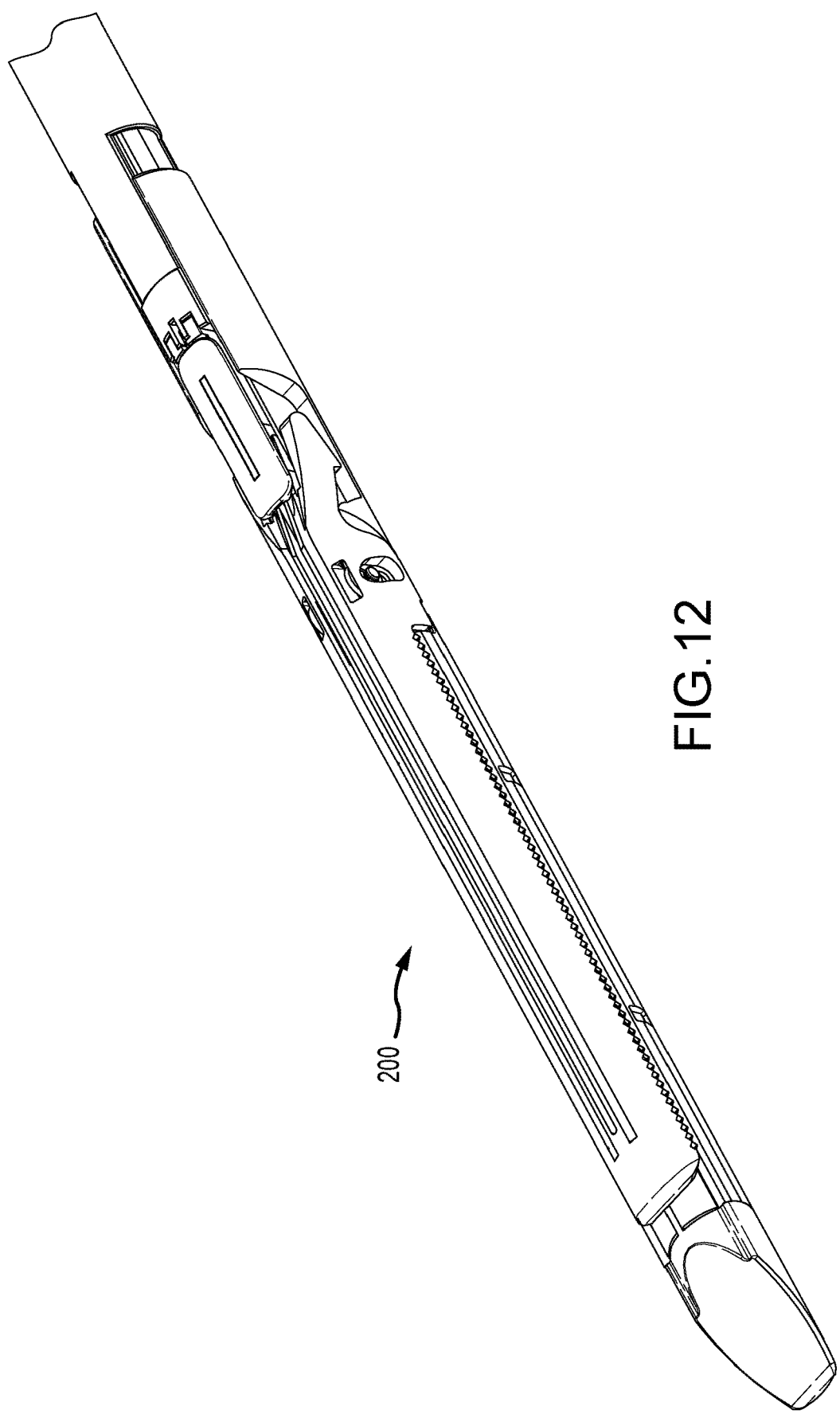
FIG. 12 is a perspective view of a surgical stapler suitable for use with the assembly of FIG. 1 or FIG. 3, or the component of FIG. 10.

FIG. 12 illustrates a surgical stapler 200 according to some embodiments.

Figure 13:
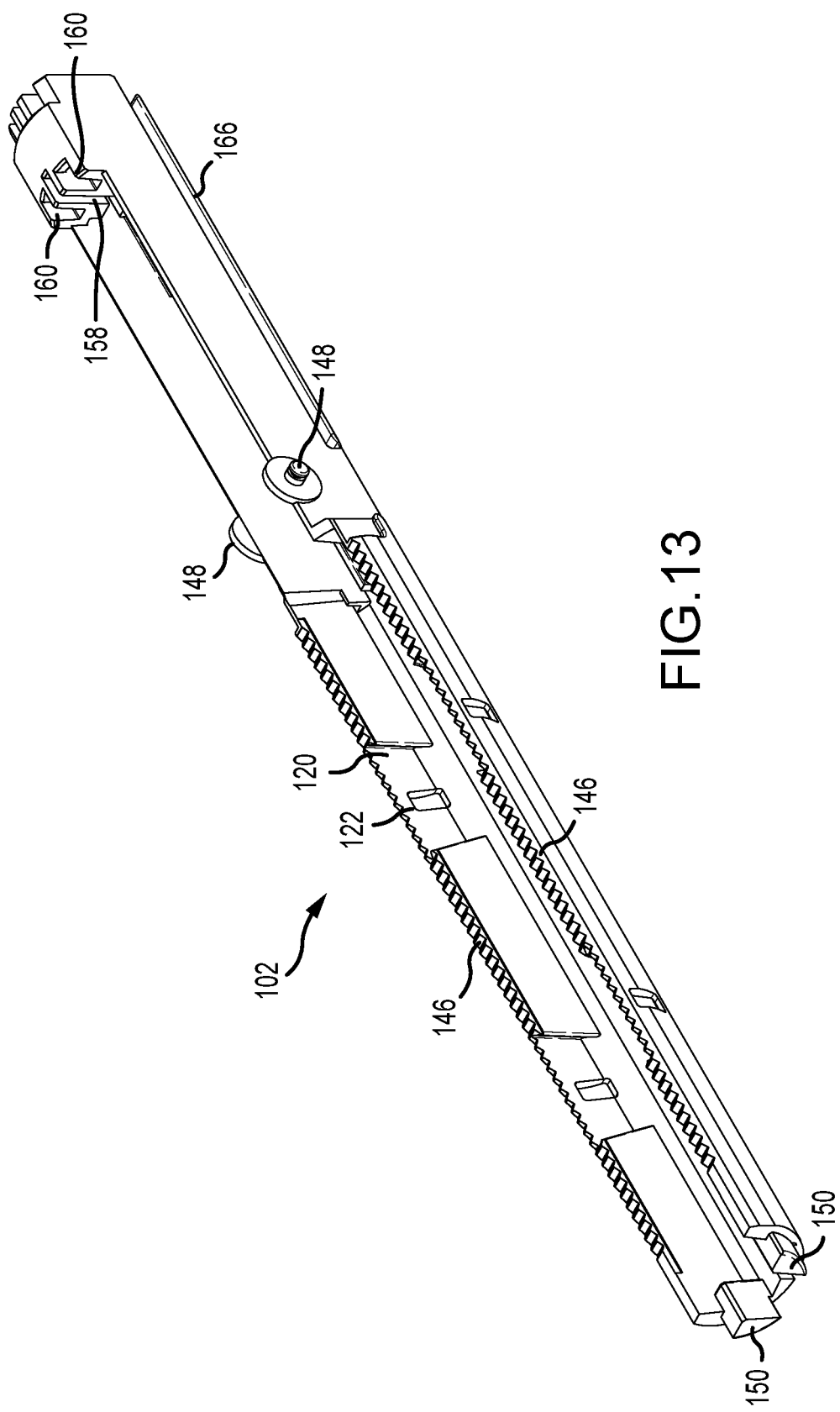
FIG. 13 is a perspective view of a housing for a cartridge assembly such as the assembly illustrated in FIG. 1.

As most clearly illustrated in FIG. 13, in some embodiments, the cartridge housing 102 may include a texturized surface having one or more ridges 146 for securely gripping tissue positioned between the cartridge housing 102 and an anvil. The anvil may also include a texturized surface with ridges for gripping tissue. The cartridge housing 102 may also include a mounting feature 148 for coupling an anvil thereto. The cartridge housing 102 may also include a cap engagement feature(s) 150, which may include a flange for engaging the distal cap 108.

Figure 14:
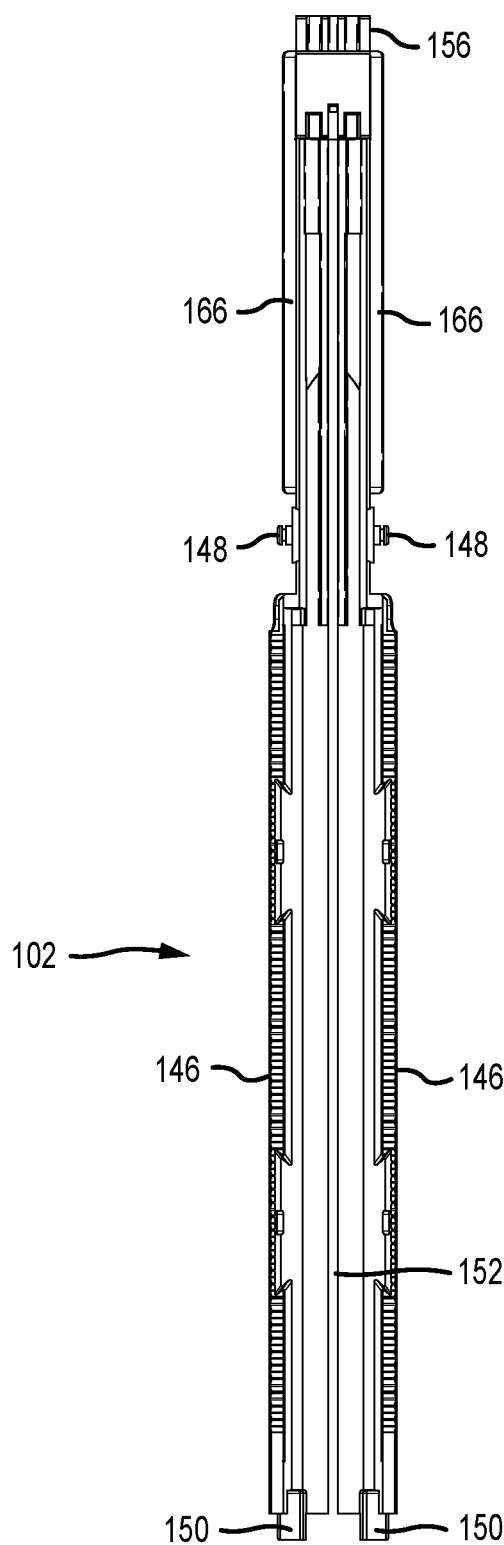
FIG. 14 is a top view of the housing illustrated in FIG. 13.

As illustrated in FIG. 14, the cartridge housing may also include an i-beam slot 152, aligned with the knife channel 118, to allow translation of an i-beam having an upper i-beam portion 182, a knife 180, and a lower i-beam portion 184. (See e.g. FIG. 28.) A relief 158 (see FIG. 13) may also provide for seating of portions of the i-beam.

Figure 15:
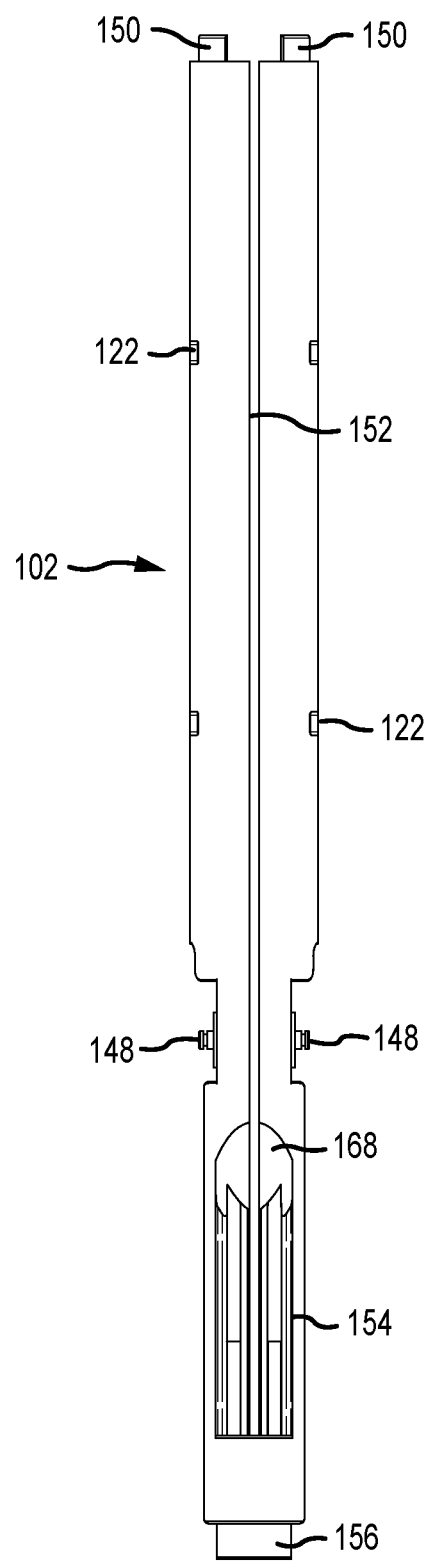
FIG. 15 is a bottom view of the housing illustrated in FIG. 13.
Figure 16:
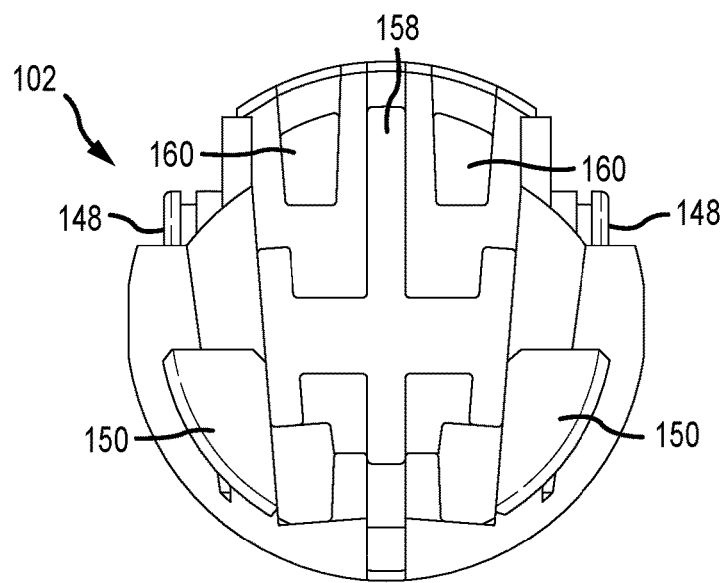
FIG. 16 is a distal end view of the housing illustrated in FIG. 13.

As illustrated in FIG. 15, a proximal portion of the housing 102 may also include a recess(s) 154 to seat the lower i-beam portion 184 in a compacted configuration relative to the upper i-beam portion 182. In some embodiments, the proximal portions of the housing and the cartridge portions 104, 106 may be configured to seat the upper and lower i-beam portions 182, 184 in a compacted configuration. The proximal portion of the housing 102 may also include a coupling feature 156 for attaching the housing 102 to a shaft assembly.

Returning again to FIG. 13, recesses 160 may receive the cartridge tabs 136 and, in coordination with other features may prevent the cartridge 104 from lifting or moving away from the housing 102 during a firing of staples.

Figure 17:
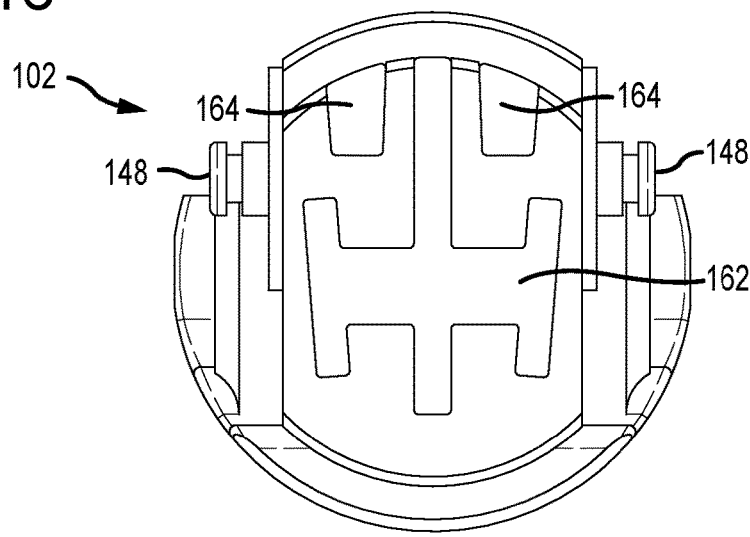
FIG. 17 is a proximal end view of the housing illustrated in FIG. 13.

Turning now to FIG. 17, a slot for actuator for staple pushers and the i-beam.may be provided. In some embodiments, the slot 162 is asymmetric. In some embodiments, the slot 162 is configured to house or guide the actuator(s) at an angle relative to the knife channel 118. In some embodiments, the floor of the center channel is configured to limit the i-beam (rigid or expanding) from translating downward. In some embodiments, the top of the channel may be configured to limit the i-beam from translating upward (not illustrated).

Much like recess 160, recesses 164 are cores for forming a portion of features in during molding.

Figure 18:
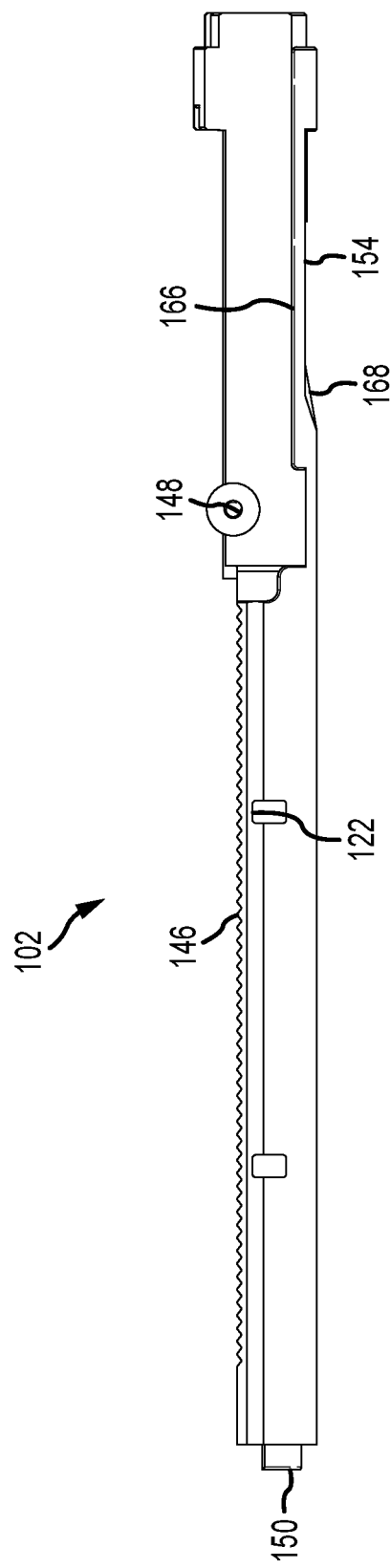
FIG. 18 is a side view of the housing illustrated in FIG. 13.
Figure 19:
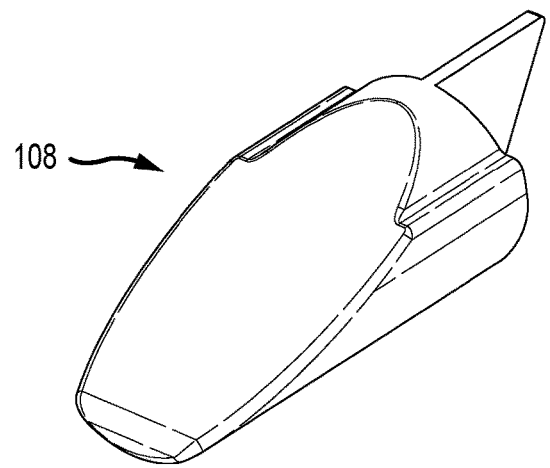
FIG. 19 is a perspective view of a cap for a cartridge assembly such as the assembly illustrated in FIG. 1 or the stapler illustrated in FIG. 12.
Figure 20:
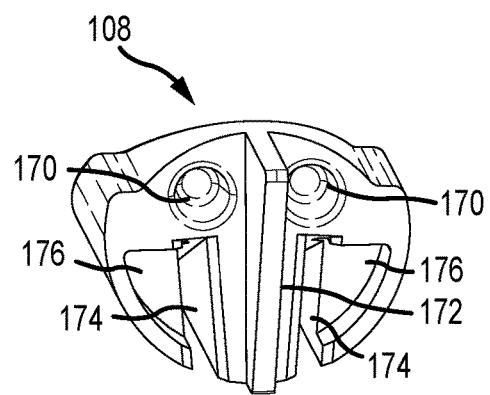
FIG. 20 is a proximal perspective view of the cap illustrated in FIG. 19.
Figure 21:
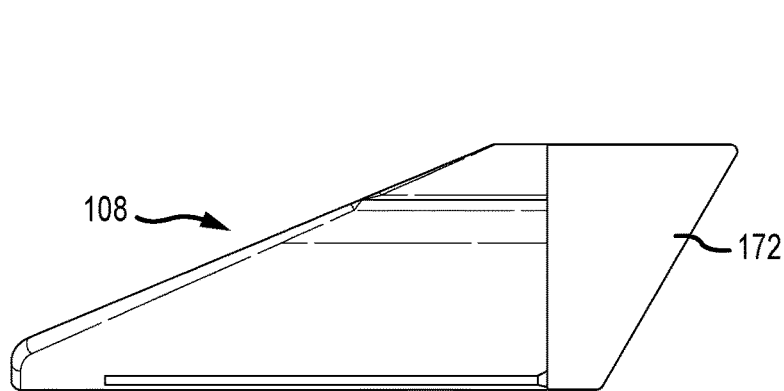
FIG. 21 is a side view of the cap illustrated in FIG. 19.
Figure 22:
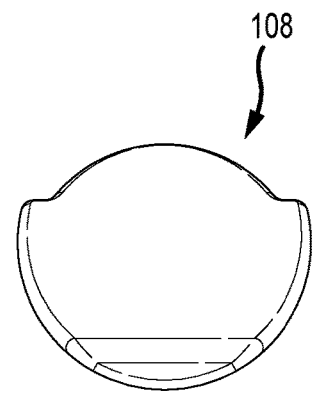
FIG. 22 is a distal end view of the cap illustrated in FIG. 19.
Figure 23:
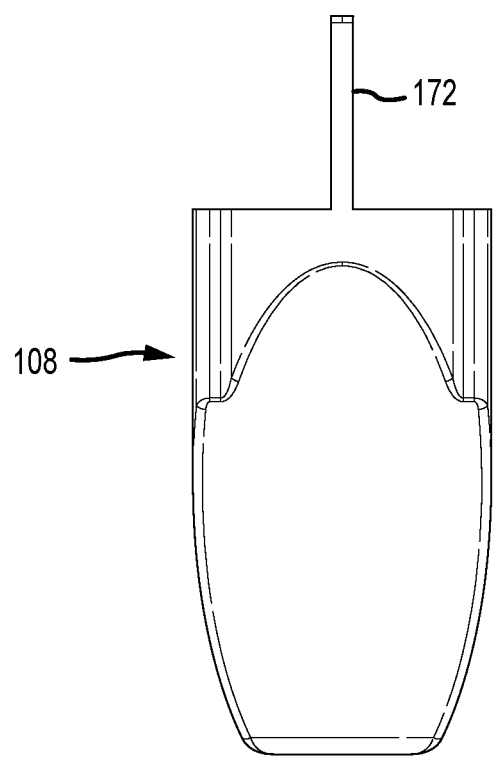
FIG. 23 is a top view of the cap illustrated in FIG. 19.
Figure 24:
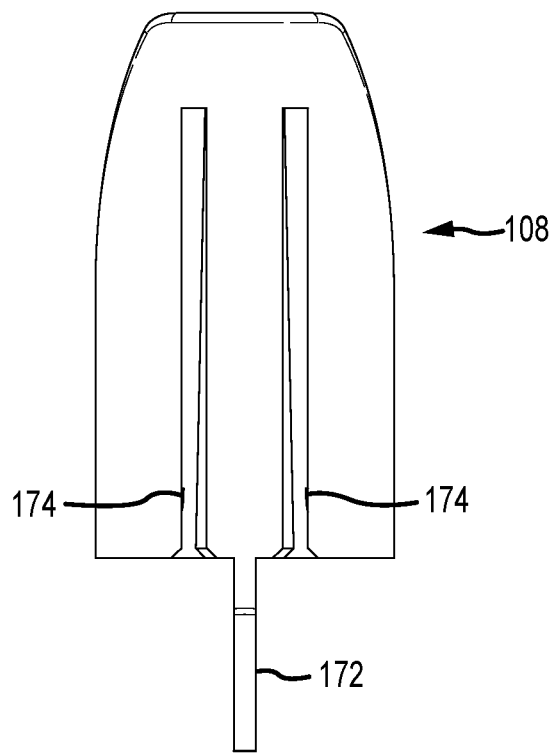
FIG. 24 is a bottom view of the cap illustrated in FIG. 19.
Figure 25:
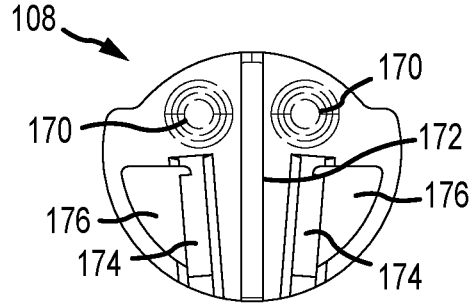
FIG. 25 is a proximal end view of the cap illustrated in FIG. 19.

As illustrated most clearly in FIG. 18, the housing 102 may also have a flange surface 166 for guiding an anvil actuator to open or close the anvil, and a ramp surface 168 for guiding the lower i-beam portion 184 between the compacted configuration and an expanded configuration as the i-beam translates distally and/or proximally.

Turning now to FIGS. 19-25, the distal cap 108 may have a recess(s) 170 for engaging the cartridge portion(s) 104, 106, and a ridge 172 for maintaining the cartridge portion(s) 104, 106 in a spaced-apart configuration to provide the knife channel 118. The cap 108 may also have one or more cam receiving slots 174 and one or more housing engagement features 176 such as recesses.

Figure 26:
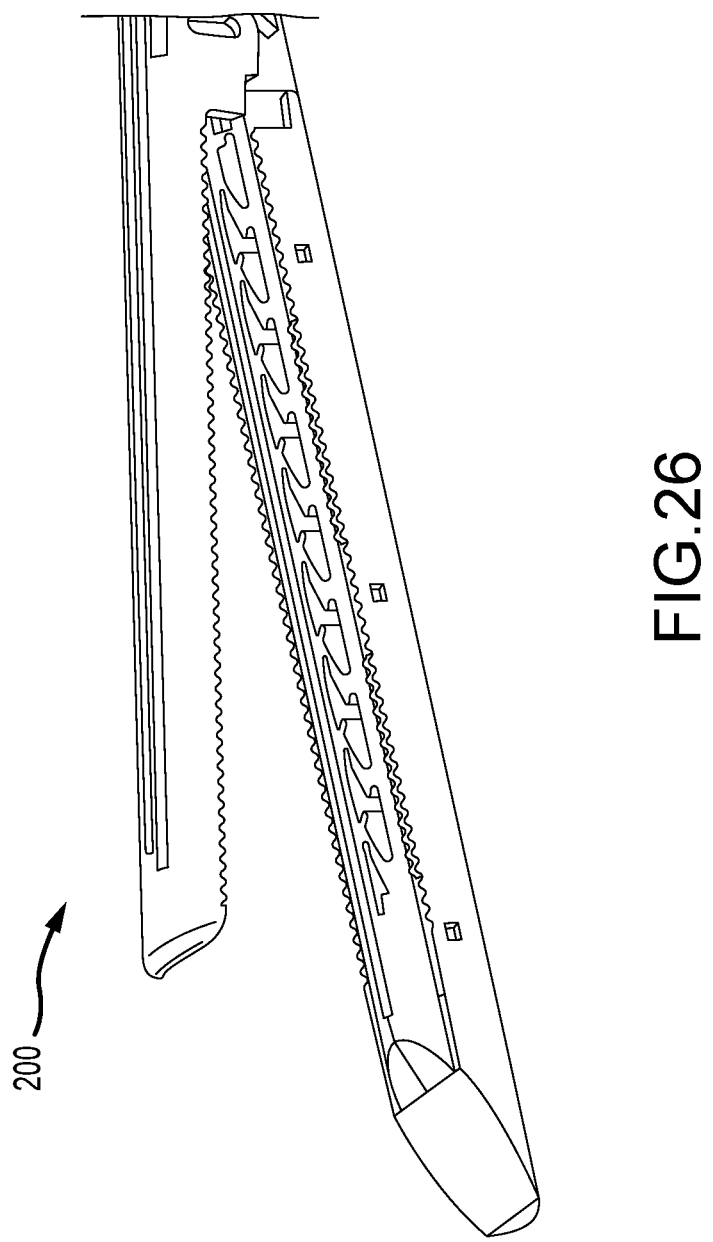
FIG. 26 is a perspective view of an exemplary stapler.
Figure 27:
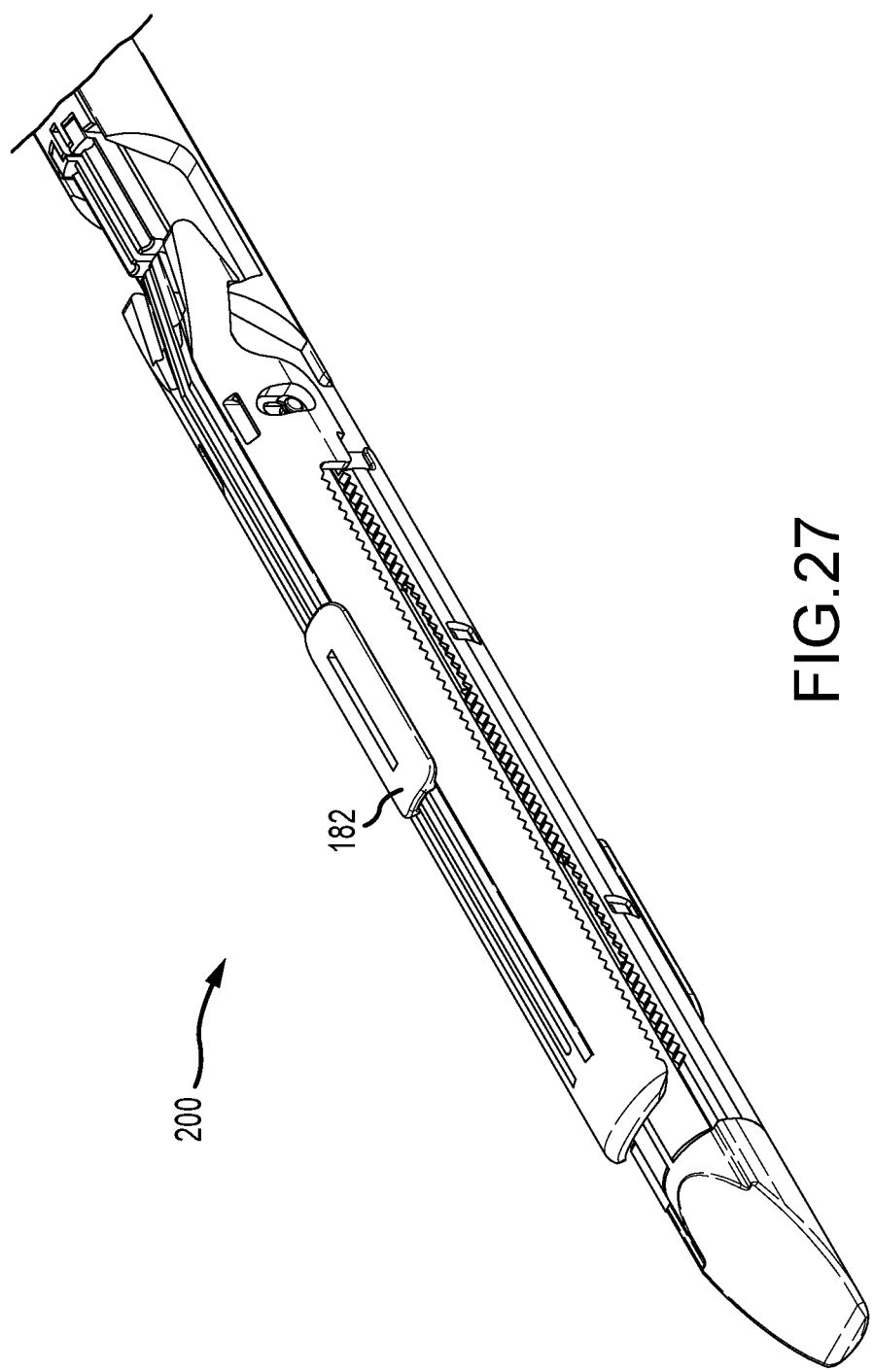
FIG. 27 is a perspective view of an exemplary stapler.

FIG. 26 and FIG. 27 illustrate a stapler 200 with the i-beam having an upper i-beam portion 182.

Figure 28:
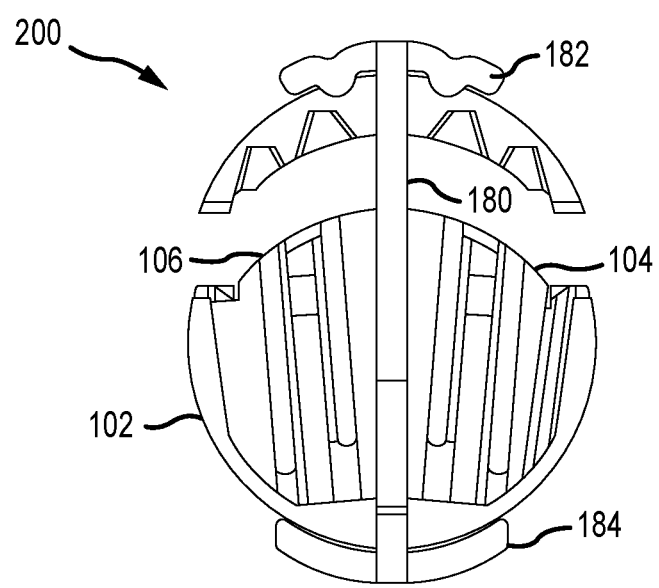
FIG. 28 is a section view of an exemplary stapler.

As illustrated in FIG. 28, the stapler 200 may have an i-beam with an upper i-beam portion 182, a knife portion 180, and a lower i-beam portion 184.

Figure 29:
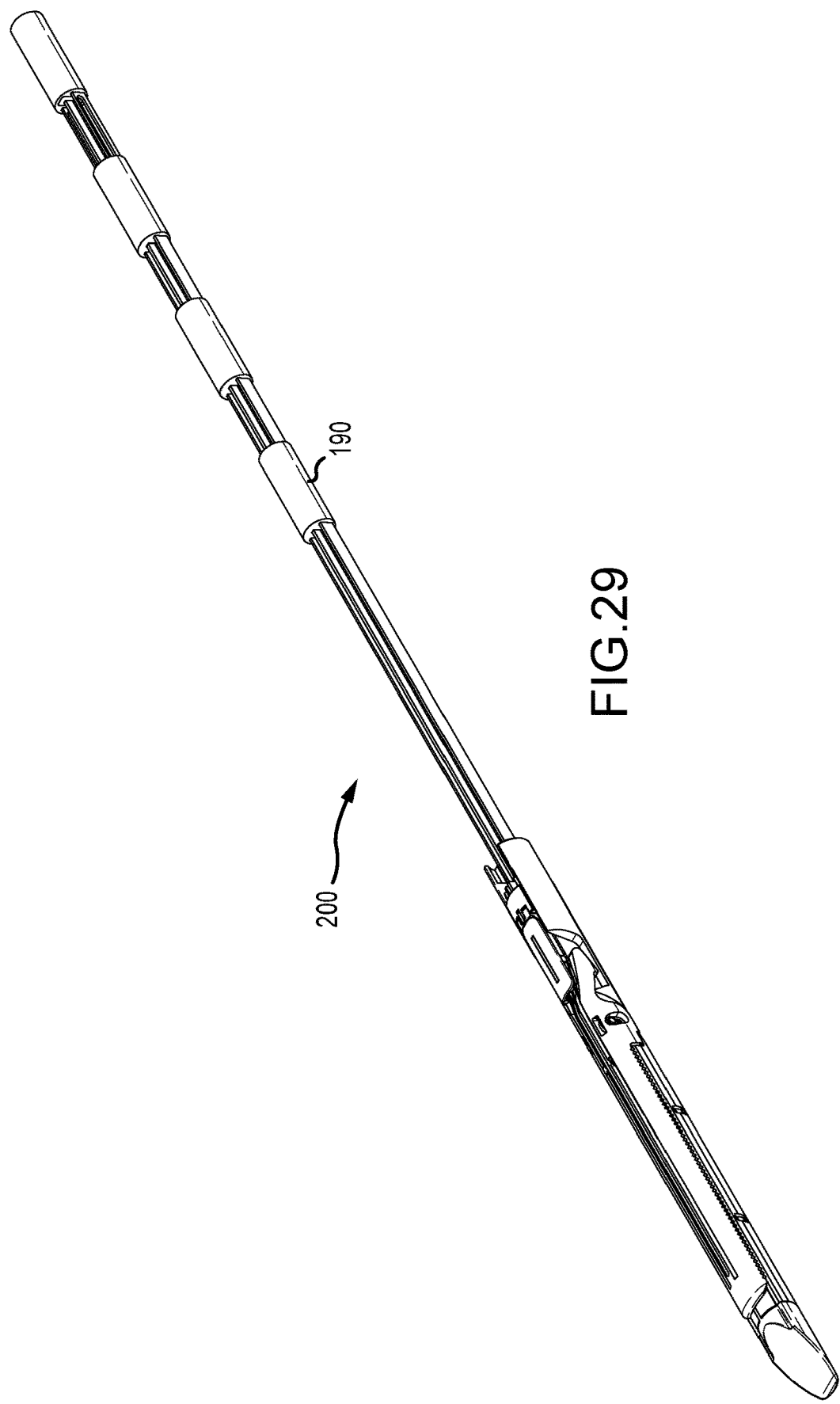
FIG. 29 is a perspective view of an exemplary stapler.
Figure 30:
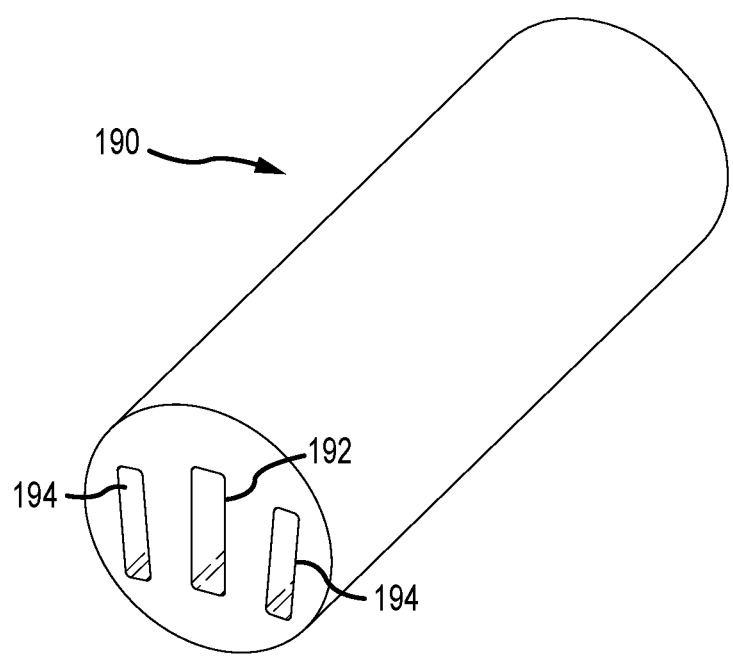
FIG. 30 is a perspective view of a spacer suitable for use in an exemplary stapler.
Figure 31:
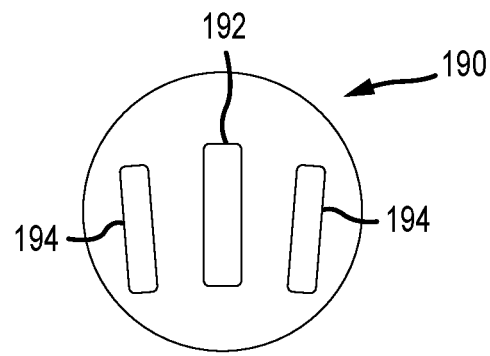
FIG. 31 is a section view of the spacer illustrated in FIG. 30.

In some embodiments, and as most clearly illustrated in FIG. 29, FIG. 30, and FIG. 31, the stapler 100, 200 may include telescoping sections 190 to reduce friction during activation of one or more driving mechanisms, such as is described in commonly-assigned U.S. Pat. No. 8,517,240, which issued on Aug. 27, 2013, the entire disclosure of which is hereby incorporated by reference for all proper purposes.

In some embodiments, the sections 190 may include a slot 192 for a knife or i-beam, or i-beam actuator and two slots 194 for cam actuators.

Figure 32:
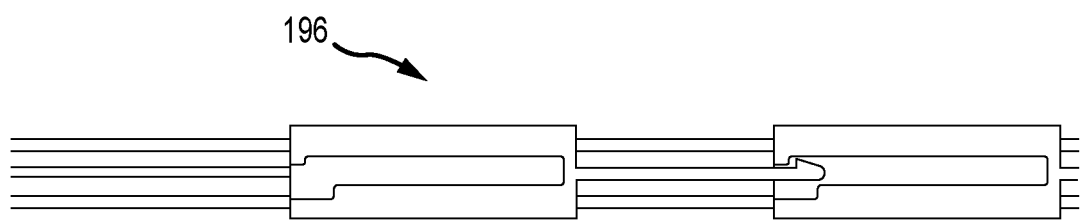
FIG. 32 is a top view of a spacer suitable for use in an exemplary stapler.
Figure 33:
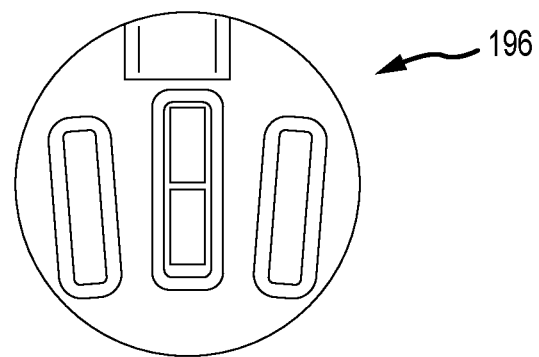
FIG. 33 is a section view of the spacer illustrated in FIG. 32.

In some embodiments, the sections 196 may nest together, as illustrated in FIG. 32 and FIG. 33.

Figure 34:
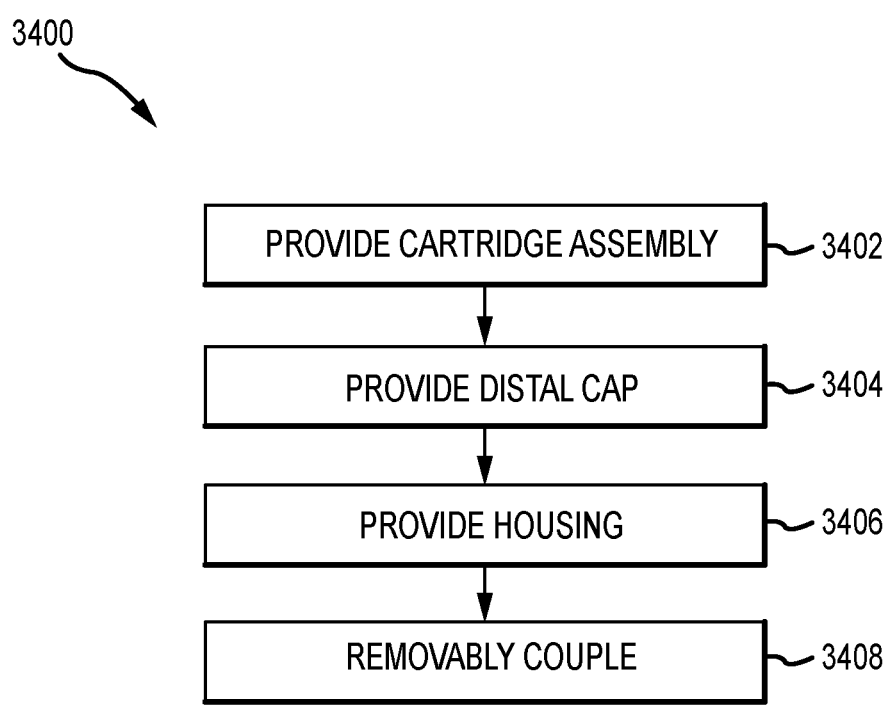
FIG. 34 is a flowchart of a method.

Turning now to FIG. 34, a method 3400 of making a surgical stapler may include providing 3402 a cartridge assembly. The cartridge assembly may include a first cartridge portion and a second cartridge portion as described herein. The method 3400 may include providing 3404 a distal cap. The distal cap may be substantially as described herein. The method 3400 may include providing 3406 a housing. The housing may be substantially as described herein. The method 3400 may include removably coupling 3408 the first cartridge portion and the second cartridge portion using the distal cap, to form a knife channel between the cartridge portions. The distal cap described herein may be used.

Providing a cartridge assembly may include providing a cartridge assembly wherein at least one of the first cartridge portion or the second cartridge portion comprises a movable member adjacent the knife channel, the movable member configured to be displaced by a knife translating in the knife channel to widen at least a portion of the knife channel.

In some embodiments, the first cartridge portion and the second cartridge portion each have a distal portion housing the respective staple slot, and a recess between the distal portion and the proximal portion, the recess configured to receive a proximal portion of an anvil rotatably coupled to the assembly.

In some embodiments, at least one of the cartridge portions has an inner wall for forming the knife channel, and the slot is configured to house a staple at a non-parallel angle to the inner wall.

Figure 4:
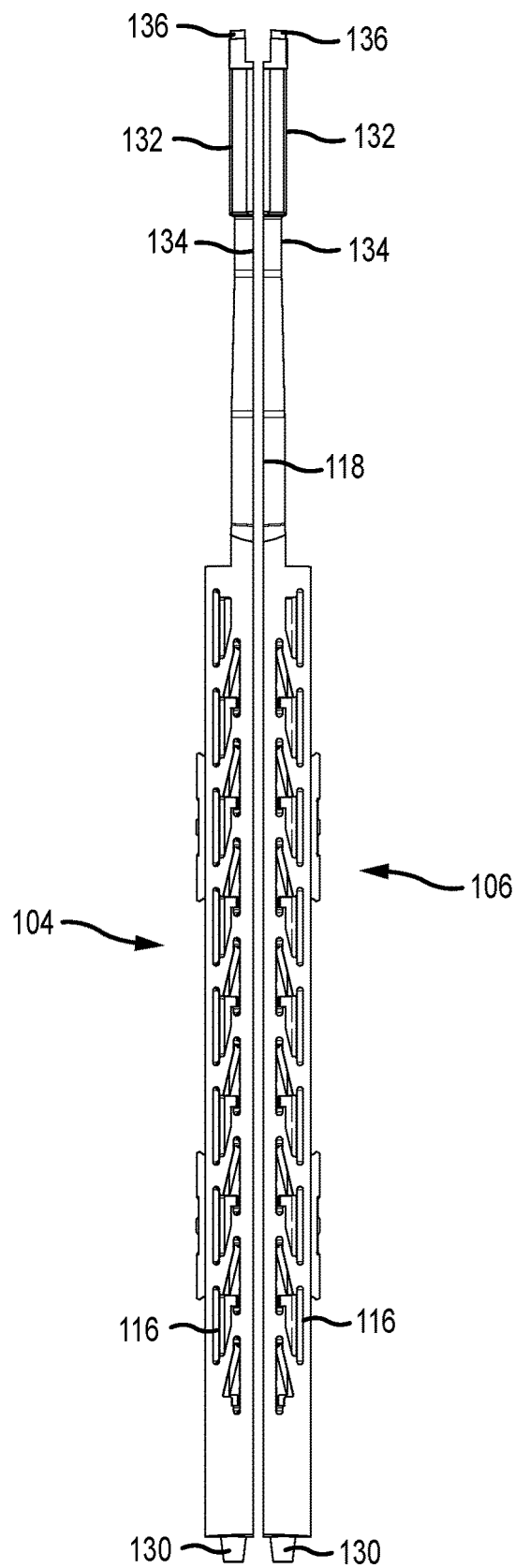
FIG. 4 is a top view of the assembly in FIG. 3.
Figure 5:
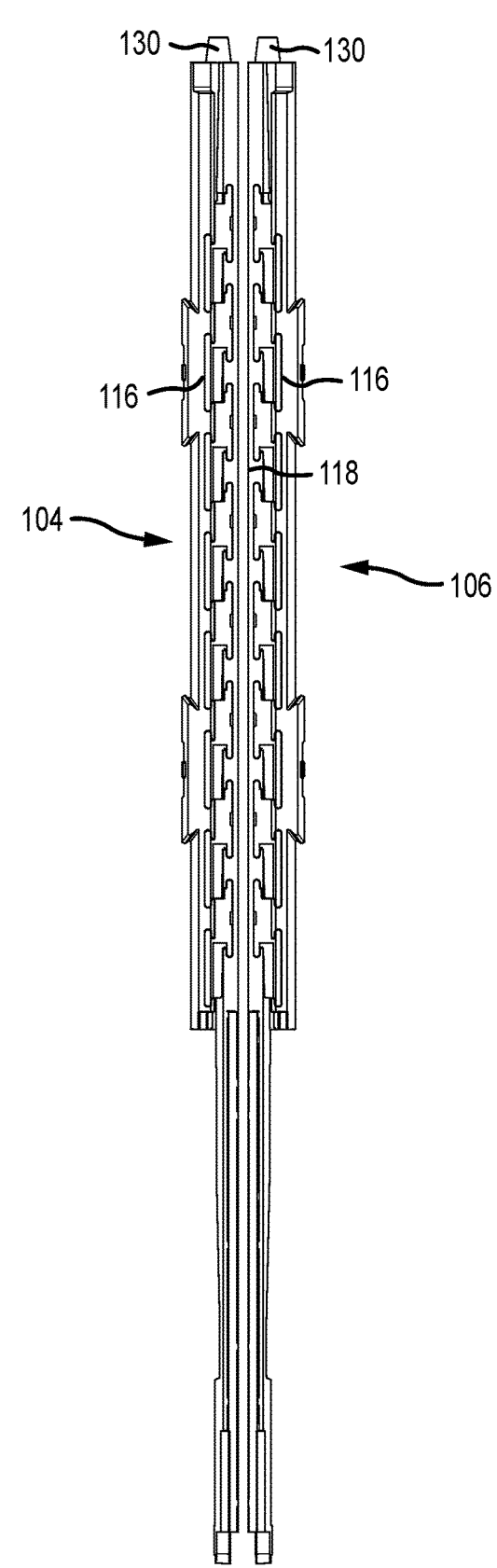
FIG. 5 is a bottom view of the assembly in FIG. 3.

As illustrated most clearly in FIG. 4 and FIG. 5, a proximal portion of the cartridge portion(s) 104, 106 may be narrower than a distal portion, so as to provide space for the anvil.

In some embodiments, a cartridge assembly for a surgical stapler has a first cartridge portion and a second cartridge portion, as illustrated in FIG. 1. Each of the first and second cartridge portions may have an upper portion for engaging tissue, a lower portion, and a slot extending from the upper portion to the lower portion. The slot may house a staple and/or a staple pusher. The second cartridge portion may be removably couplable to the first cartridge portion to form a knife channel between the first and second cartridge portion.

Turning briefly to FIG. 10 and FIG. 11, the knife channel may have an upper portion and a lower portion. A first movable member in the first cartridge portion and a second movable member in the second cartridge portion may form the lower portion of the knife channel The first movable member and the second movable member may be movable to widen the lower portion of the knife channel The first and second movable members may be movable into space previously occupied by first and second staple pushers. The first and second movable members may be resilient members. In some embodiments, the first and/or second movable member(s) may move in a manner that supports the respective staple pusher(s) and/or otherwise assist in driving the respective staple pusher(s) within or through the respective slot.

In some embodiments, a cartridge for a surgical stapler is provided. The cartridge may have an upper portion for engaging tissue, a lower portion, and a slot extending from the upper portion to the lower portion, the slot configured to house a staple and a staple pusher. The slot may have a resilient member forming at least a portion of a wall of the slot. The resilient member may be movable to adjust a size of a portion of the slot. The resilient member may be movable to adjust a size of a portion of a knife channel positioned near the slot.

As illustrated most clearly in FIG. 1 and FIG. 3, in some embodiments, at least one of the first cartridge portion or the second cartridge portion has a flange configured to engage a flange in a cartridge housing to align the assembly with the cartridge housing.

In some embodiments, and as illustrated in FIG. 1, the first cartridge portion and the second cartridge portion may be fixed together by the cartridge housing.

In some embodiments, and as illustrated in FIGS. 1-3, the first cartridge portion and the second cartridge portion may be fixed together by a cap engaging a distal portion of each of the first and second cartridge portions. In some embodiments, the assembly having the cap and first and second cartridge portions may be assembled. Thereafter, pushers may be added to the assembly, followed by staples. In some embodiments, pushers may be added prior to fixing the cartridge portions together. In some embodiments, both the pushers and the staples may be added prior to fixing the cartridge portions together. In some embodiments, the cap may be coupled to the first and second cartridge portions. In some embodiments, the cap may be coupled to the housing. In some embodiments, the cap may be coupled to the housing and one or both cartridge portions.

Returning now to FIG. 1, the first cartridge portion and the second cartridge portion each may have a distal portion housing the respective slots, a proximal portion, and a tapered wall therebetween, to accommodate portions of the anvil.

In some embodiments, a cartridge assembly for a surgical stapler may be provided with a first cartridge portion and a second cartridge portion removably couplable to the first cartridge portion to form a channel therebetween. Each of the first and second cartridge portions may have an adjustable staple pusher slot. Each of the adjustable staple pusher slots may have a movable member designed to selectively widen portions of the channel The adjustable staple pusher slots may widen the channel in response to force applied by a member passing therebetween. The member may be a cutting mechanism for the surgical stapler. The movable members may be resilient members and the adjustable staple pusher slots may be deformable staple pusher slots.

The adjustable staple pusher slots may be configured to physically support the pushers so they do not fall towards or into the channel, or otherwise become dislodged. In some embodiments, the adjustable staple pusher slots may improve or promote material flow in the molding tool during manufacture of the cartridge portion(s) 104, 106.

In some embodiments, the stapler may include one or more cams that, upon activation, push the staple pushers against the staples to cause the staples to couple tissue. Thereafter, either in response to a second activation or the same activation with a delayed response, a cutting mechanism may pass into or through the channel As the cutting mechanism moves, it may move the movable members. Where the movable members are provided by resilient members, the cutting mechanism may deform or move the resilient members.

In some embodiments, upon an activation, the movable members may be moved to widen the channel by the leading edge of a flange that is a feature of the cutting mechanism. In some embodiments, the cutting mechanism may include an expandable I-beam that has an upper I-beam portion, a lower I-beam portion, and a cutting portion. The lower I-beam portion may include a flange surface or a leading surface that engages the movable member(s) during firing to allow completion of a cutting action. Because the movable member(s) must be displaced prior to passing of the knife or cutting mechanism, in the event that a stapling action is not completed, the knife cannot be driven into a region of tissue that is not stapled. That is, the movable members are prevented from widening the channel if the staple pusher(s) are not displaced by way of a successful stapling action, thereby preventing the risk of unstapled tissue being severed. In some embodiments, the movable members are not movable prior to displacement of the staple pusher(s).

In some embodiments, the movable members may include a hinge feature to bias or ease movement in a desired direction to widen the channel In some embodiments, the hinge feature may be a living hinge. This may also reduce friction between the cutting mechanism and the cartridge portions, thereby enabling overall dimensions of the stapler to be reduced.

In some embodiments, the movable members may include a breakaway feature to widen the channel.

In some embodiments, the movable members may operate as an aid to initiate movement of the pusher(s), essentially "priming" the position of the pusher(s) so that camming mechanism may move below the pushers to drive them (and the staples) towards the upper surface of the stapler. This feature may further reduce friction between the moving and non-moving components of the stapler, and, again, allow for smaller or less-strong components to be utilized. This "priming" feature may include a flange surface on the leading end of the lower I-beam portion, which may fold the cartridge wall or movable member(s) under the staple pusher(s), forcing the staple pusher(s) upward before the cam passes into the space.

FIG. 6 and FIG. 7 illustrate cartridge cross-sections showing two configurations of the movable or resilient members forming the knife channel. In some embodiments, the movable members may be formed by providing a thin-wall portion that is deformable, even if the base material is not usually considered a deformable material, such as by providing a resilient member. In some embodiments, a notch may be provided so as to effectively provide a hinge feature.

As most clearly illustrated in FIG. 1 and FIG. 26, some embodiments of the stapler may include tissue gripping features 146 on the movable anvil, the outer housing, and/or one or both of the cartridge portions. The tissue gripping features may include ridges, a roughened surface, raised teeth, or other features to effectively grip tissue to prevent movement of the tissue during the procedure. Specifically, the gripping features may be configured to prevent tissue from extruding out the distal end prior to being secured by staples.

FIG. 1 illustrates an exemplary cartridge assembly with a stapler housing and cap, as described according to some embodiments.

With reference now to FIG. 28, features suitable for use in the stapler illustrated in FIG. 1 and previously described herein are described. As illustrated, the I-beam may include one or more raised protrusions that engage respective recess(es) or channel(s) in the anvil, so as to provide a guiding feature or stabilizing feature for function between the I-beam and the anvil. In some embodiments, the I-beam clamp may constrain the split anvil laterally and/or vertically. In some embodiments, the recess(es) or channel(s) in the anvil guide the I-beam clamp or upper I-beam portion and maintain its alignment with the lower I-beam member. Those skilled in the art will recognize that the protrusions may be on the anvil and the recess(es) may be on the I-beam portion. Those skilled in the art will also recognize that the guiding or stabilizing feature may be an interface between the lower I-beam portion (instead of the upper I-beam portion) and the housing. That is, the stapler may include a flange engagement between the I-beam assembly and at least one of the anvil, the housing, or the cartridge. The flange engagement may be configured to limit lateral movement of the I-beam assembly relative to the anvil, housing, cartridge, and/or longitudinal axis of the stapler. The flange engagement may be configured to stabilize the anvil, cartridge, and/or housing.

Turning now to FIGS. 29-33, in some embodiments, the stapler may include a plurality of telescoping spacers. These spacers may move between an extended configuration and a collapsed configuration. The spacers may be configured to reduce friction between moving features of the stapler. The spacers may function substantially as described in U.S. Pat. No. 9,750,497, which issued on Sep. 5, 2017 to Mata et al., the entire contents of which are incorporated herein by reference.

As illustrated in FIG. 30 and FIG. 33, in some embodiments, the spacer(s) may include a center slot to house or receive both I-beam shanks and/or to hold the two shanks together vertically. In addition, the spacer(s) may assist in preventing buckling.

A method of making a surgical stapler may include providing a cartridge assembly according to the cartridge assembly embodiments described herein, positioning the cartridge assembly in a cartridge housing, and providing an anvil. The method may include coupling the anvil and the cartridge housing such that the anvil is movable relative to the cartridge housing and cartridge assembly between an open position and an approximated position for clamping tissue therebetween.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, by way of example only, the disclosure of an actuator should be understood to encompass disclosure of the act of actuating—whether explicitly discussed or not—and, conversely, were there only disclosure of the act of activating, such a disclosure should be understood to encompass disclosure of an activating mechanism. Such changes and alternative terms are to be understood to be explicitly included in the description.

The previous description of the disclosed embodiments and examples is provided to enable any person skilled in the art to make or use the present invention as defined by the claims. Thus, the present disclosure is not intended to be limited to the examples disclosed herein. Various modifications to these embodiments may be readily apparent to those skilled in the art, and the generic principles defined herein may be applied to other embodiments without departing from the scope of the invention as claimed.

What is claimed is:

1. A cartridge assembly for a surgical stapler, comprising:
a first cartridge portion; and
a second cartridge portion; wherein each of the first and second cartridge portions has an upper surface for engaging tissue, and a slot configured to house a staple;
a proximal portion of each of the first and second cartridge portions has a guide portion having at least one of a channel or a protrusion for guiding at least a portion of an i-beam; and
the second cartridge portion is removably couplable to the first cartridge portion to form a channel between the first and second cartridge portion; and wherein
at least one of the first cartridge portion or the second cartridge portion comprises a movable member adjacent the channel, the movable member configured to be displaced by a knife translating in the channel to widen at least a portion of the channel.

2. The assembly of claim 1, wherein:
the movable member is a resilient member.

3. The assembly of claim 1, wherein:
at least one of the first cartridge portion or the second cartridge portion has a flange configured to engage a flange in a cartridge housing to align the assembly with the cartridge housing.

4. The assembly of claim 1, wherein:
the first cartridge portion and the second cartridge portion are configured to be fixed together by a cartridge housing.

5. The assembly of claim 1, wherein:
the first cartridge portion and the second cartridge portion are configured to be fixed together by a cap engaging a distal portion of each of the first and second cartridge portions.

6. The assembly of claim 1, wherein:
the first cartridge portion and the second cartridge portion each have a distal portion housing the respective slot, and a recess between the distal portion and the proximal portion, the recess configured to receive a proximal portion of an anvil rotatably coupled to the assembly.

7. The assembly of claim 1, wherein:
at least one of the first or second cartridge portions has an inner wall for forming the channel; and
the slot in the at least one of the first or second cartridge portions is configured to house a staple at a non-parallel angle to the inner wall.

8. A surgical stapler, comprising:
a cartridge assembly, the cartridge assembly having a first cartridge portion; and
a second cartridge portion, wherein each of the first and second cartridge portions has an upper surface for engaging tissue, and a slot configured to house a staple, a proximal portion of each of the first and second cartridge portions has a guide portion having at least one of a channel or a protrusion for guiding at least a portion of an i-beam, and the second cartridge portion is removably couplable to the first cartridge portion to form a channel between the first and second cartridge portion;
a distal cap; and
a housing; wherein
the distal cap and the housing removably couple the first cartridge portion and the second cartridge portion to form the channel therebetween; and wherein
at least one of the first cartridge portion or the second cartridge portion comprises a movable member adjacent the channel, the movable member configured to be displaced by a knife translating in the channel to widen at least a portion of the channel.

9. The stapler of claim 8, wherein:
the movable member is a resilient member.

10. The stapler of claim 8, wherein:
the first cartridge portion and the second cartridge portion each have a distal portion housing the respective slot, and a recess between the distal portion and the proximal portion, the recess configured to receive a proximal portion of an anvil rotatably coupled to the assembly.

11. The stapler of claim 8, wherein:
the slot in at least one of the first or second cartridge portions is configured to house a staple at a non-parallel angle to the channel.

12. A method of making a surgical stapler, comprising:
providing a cartridge assembly, the cartridge assembly having a first cartridge portion, and a second cartridge portion, wherein each of the first and second cartridge portions has an upper surface for engaging tissue, and a slot configured to house a staple, a proximal portion of each of the first and second cartridge portions has a guide portion having at least one of a channel or a protrusion for guiding at least a portion of an i-beam, and the second cartridge portion is removably couplable to the first cartridge portion to form a channel between the first and second cartridge portion;
providing a distal cap;
providing a housing;
using the distal cap and the housing to removably couple the first cartridge portion and the second cartridge portion and form the channel therebetween; wherein the providing a cartridge assembly comprises providing a cartridge assembly wherein at least one of the first cartridge portion or the second cartridge portion comprises a movable member adjacent the channel, the movable member configured to be displaced by a knife translating in the knife channel to widen at least a portion of the knife channel.

13. The method of claim 12, wherein:
the first cartridge portion and the second cartridge portion each have a distal portion housing the respective slot, and a recess between the distal portion and the proximal portion, the recess configured to receive a proximal portion of an anvil rotatably coupled to the assembly.

14. The method of claim 12, wherein:
at least one of the first or second cartridge portions has an inner wall for forming the channel; and
the slot in the at least one of the first or second cartridge portions is configured to house a staple at a non-parallel angle to the inner wall.

\* \* \* \* \*